(12) United States Patent
Dawson

(10) Patent No.: US 9,489,935 B2
(45) Date of Patent: Nov. 8, 2016

(54) AMBIENT GAS FLOW ALARM

(71) Applicant: PROMETHEUS MEDICAL INNOVATIONS LLC, Waterford, PA (US)

(72) Inventor: Randy J. Dawson, Waterford, PA (US)

(73) Assignee: PROMETHEUS MEDICAL INNOVATIONS LLC, Waterford, PA (US)

( * ) Notice: Subject to any disclaimer, the term of this patent is extended or adjusted under 35 U.S.C. 154(b) by 145 days.

(21) Appl. No.: 14/406,979

(22) PCT Filed: Jun. 11, 2013

(86) PCT No.: PCT/US2013/045112
§ 371 (c)(1),
(2) Date: Dec. 10, 2014

(87) PCT Pub. No.: WO2013/188360
PCT Pub. Date: Dec. 19, 2013

(65) Prior Publication Data
US 2015/0170630 A1    Jun. 18, 2015

Related U.S. Application Data

(60) Provisional application No. 61/658,210, filed on Jun. 11, 2012.

(51) Int. Cl.
*G10K 5/00* (2006.01)
*G08B 3/02* (2006.01)
(Continued)

(52) U.S. Cl.
CPC ............ *G10K 5/00* (2013.01); *A61M 16/0051* (2013.01); *F17D 5/005* (2013.01); *G01M 3/26* (2013.01); *G08B 3/02* (2013.01); *G08B 3/06* (2013.01); *G08B 21/12* (2013.01); *G08B 21/14* (2013.01)

(58) Field of Classification Search
CPC ... A61M 16/00; A61M 16/0051; F17D 5/00; G08B 3/00; G08B 3/02; G08B 3/06; G08B 21/12; G08B 21/14; G08B 21/16; G10K 5/00; G10K 5/02; G01M 3/26
USPC ......... 116/70, 112, 264; 128/202.22, 205.23; 137/557
See application file for complete search history.

(56) References Cited

U.S. PATENT DOCUMENTS 1,671,578 A    5/1928  Goodstone
2,376,971 A *  5/1945  Kleit .................... A61M 16/06
                                                    116/137 R
(Continued)

FOREIGN PATENT DOCUMENTS

CA         269544 A      4/1927
CN    204193342 U *      3/2015  ............... A62B 9/00
(Continued)

OTHER PUBLICATIONS

International Search Report and Written Opinion dated Sep. 9, 2015, for International Patent Application No. PCT/US2013/045112.

*Primary Examiner* — R. A. Smith
(74) *Attorney, Agent, or Firm* — Thomas & Karceski, PC

(57) ABSTRACT

A gas flow alarm includes a main barrel with a proximal end and a distal end. The main barrel defines a gas flow direction from the proximal end to the distal end. A cap is disposed slidingly on the main barrel between a proximal position and a distal position. The proximal position of the cap defines a compressed condition of the gas flow alarm and the distal position of the cap defines an expanded condition of the gas flow alarm. A noise generating device is disposed within the main barrel. The noise generating device is adapted to generate noise from the gas flow when the gas flow alarm is in the expanded condition.

20 Claims, 15 Drawing Sheets

(51) Int. Cl.
*G08B 21/12* (2006.01)
*A61M 16/00* (2006.01)
*G01M 3/26* (2006.01)
*F17D 5/00* (2006.01)
*G08B 3/06* (2006.01)
*G08B 21/14* (2006.01)

(56) References Cited

U.S. PATENT DOCUMENTS

| | | | | |
|---|---|---|---|---|
| 3,297,255 A * | 1/1967 | Fortman | ............... | B05B 1/265 116/137 A |
| 4,602,644 A * | 7/1986 | DiBenedetto et al. | | A61B 5/087 128/207.18 |
| 4,669,415 A * | 6/1987 | Boord | ............... | A62B 9/006 116/70 |
| 4,913,103 A * | 4/1990 | Borst | ............... | F02B 77/08 123/198 D |
| 6,386,196 B1 * | 5/2002 | Culton | ............... | A61M 16/0051 116/137 R |
| 7,730,847 B1 * | 6/2010 | Redd et al. | ............... | A61M 16/08 116/112 |
| 9,186,528 B2 * | 11/2015 | Patil et al. | ............... | A62B 17/006 |

FOREIGN PATENT DOCUMENTS

| | | |
|---|---|---|
| DE | 411937 C | 4/1925 |
| FR | 2203481 A5 | 5/1974 |
| JP | S57186142 A | 11/1982 |

* cited by examiner

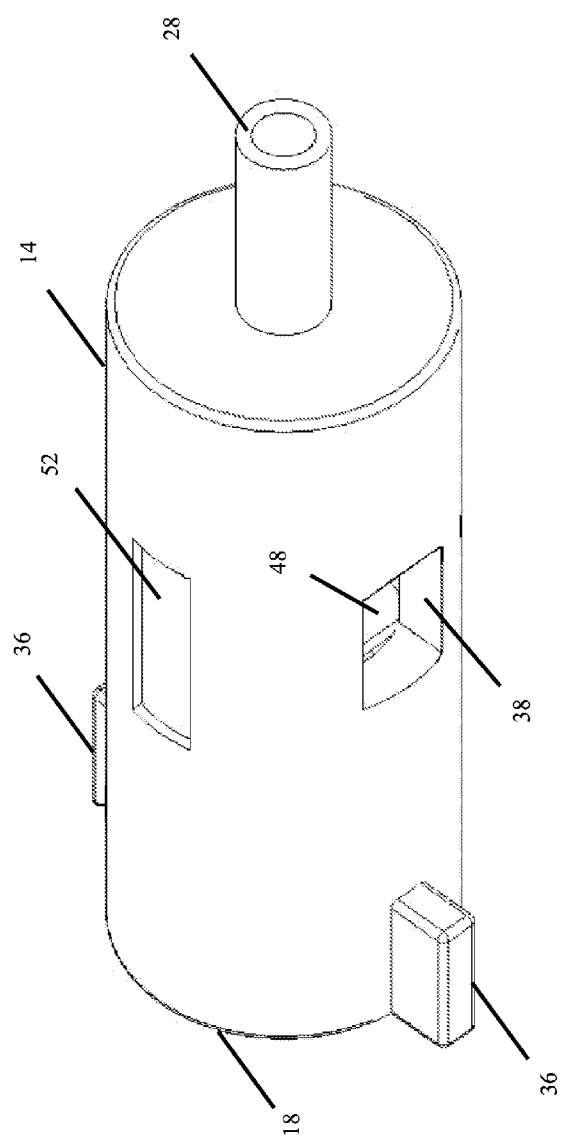

AMBIENT GAS FLOW ALARM

CROSS-REFERENCE TO RELATED PATENT APPLICATION(S)

This is a National Stage Entry into the United States Patent and Trademark Office from International Patent Application No. PCT/US2013/045112, having an international filing date of 11 Jun. 2013, and which relies for priority on U.S. Provisional Patent Application Ser. No. 61/658,210, filed on Jun. 11, 2012, the entire contents of both of which are incorporated herein by reference in their entireties.

FIELD OF THE INVENTION

The present invention relates to an apparatus that generates an alarm in response to leakage of a gas from a source of gases, such as a pressurized gas container. More specifically, the present invention concerns an apparatus that provides an audible alarm should gas leak from the pressurized gas container or should a gas line become disconnected from the pressurized gas container, among other triggering events.

DESCRIPTION OF THE RELATED ART

As should be apparent to those skilled in the art, pressurized gases are employed in any of a number of different environments. In one instance, pressurized oxygen is made available to individuals requiring higher concentrations of oxygen to address one or more medical conditions. In another instance, pressurized gases may be provided for industrial uses, such as for the purposes of welding.

As also should be apparent to those skilled in the art, it is possible that the flow of gases may be sufficiently low in volume per unit time that the flow of the gases may not be immediately perceptible to the person(s) relying on such gases. Low gas flow is common with respect to the provision of oxygen in circumstances involving medical applications, for example.

As also should be apparent to those skilled in the art, low pressure gas flow meters typically do not include safety alarms to announce that gas exiting from the gas source (i.e., a pressurized gas container such as an oxygen bottle) is being discharged into the ambient environment. In the case of oxygen, the gas is not toxic to humans, but the waste of oxygen is not preferable, as canisters of oxygen may be expensive to the patients relying on this gas.

In instances where the gas is noxious or potentially toxic to humans, the release of gases into the environment from a pressurized gas source may present other concerns, such as safety.

Inadvertent gas leaks may be caused by any of a number of different reasons. For example, a valve that with a faulty or degraded seal may permits low flow of gases from the pressurized source. Alternatively, a valve that is left partially open may allow a low flow of gases from the pressurized container.

In cases where the gases are needed to help sustain the health and life of a person (i.e., the provision of oxygen), there may be instances where the patient does not appreciate if the gas flow has been disconnected accidentally. Naturally, if the patient were to discover the inadvertent leak of gas at a time where replacement of the gas were not possible or feasible, this might present a significant problem or inconvenience to that person.

A need, therefore, has developed for a way to notify a person of a leak of one or more gases from a pressurized gas source.

SUMMARY OF THE INVENTION

The present invention provides an apparatus that initiates an alarm if there is a flow of gas from a pressurized container.

More specifically, the present invention provides for an apparatus that provides an audible alarm, should there be gas flow from a pressurized gas source, such as a gas canister (or container), compressor, or the like. Gas flow may result from a faulty valve, an open valve, or the disconnection of a tube (or pipe) normally connected to the pressurized gas source, among a wide variety of other triggering events or phenomena.

It is one aspect of the present invention, therefore, to provide an apparatus that cooperates with current, low pressure adapters used to connect tubing to a pressurized gas source to provide an alarm in the event of leakage of gases from the pressurized gas source.

In this regard, it is contemplated that the alarm of the present invention may be integrated into the current design for low-pressure gaseous flow meters.

Alternatively, the alarm of the present invention may be screwed onto flow meters currently available in the marketplace.

In one aspect of the present invention, a whistle mechanism that is integrated into the alarm that uses the actual flow of the leaking gas to make a whistling sound, thereby providing an auditory indication of leaking gases.

The audible alarm is contemplated to encourage the person to turn off the flow of the gas so as not to waste the gas. Alternatively, the alarm might indicate to a patient or caregiver that gas supply tubing has been disconnected from the pressurized gas source, requiring reconnection.

It is, therefore, one aspect of the present invention to provide a gas flow alarm with a main barrel having a proximal end and a distal end. The main barrel defines a gas flow direction from the proximal end to the distal end. The alarm also includes a cap slidingly disposed on the main barrel between a proximal position and a distal position. The proximal position of the cap defines a compressed condition of the gas flow alarm and the distal position of the cap defines an expanded condition of the gas flow alarm. The alarm further includes a noise generating device disposed within the main barrel. The noise generating device is adapted to generate noise from the gas flow when the gas flow alarm is in the expanded condition.

In one contemplated embodiment, the noise generating device is a whistle.

It is contemplated that the gas flow alarm also may include a biasing member operatively disposed between the cap and the main barrel, biasing the cap in the distal position. If so, the biasing member may be a coil spring.

It is contemplated that the proximal end of the main barrel defines a threaded portion. The threaded portion may be adapted to accommodate a diameter index safety system connector. If so, the diameter index safety system connector is contemplated to be connected to a gas source.

Another embodiment of the gas flow alarm of the present invention contemplated that a nipple is disposed at the distal end of the main barrel for connection to a gas destination. The gas destination includes tubing, which is contemplated to carry the gas to its ultimate destination. To accommodate the nipple, the cap may define an opening through a distal end thereof, permitting the nipple to protrude therethrough when the gas flow alarm is in the compressed condition.

In a further contemplated embodiment, the gas flow alarm may include a wall disposed within the main barrel, upstream of the noise generating device, for concentrating the gas flow adjacent to the noise generating device, thereby enhancing the noise generated thereby. The wall may occlude approximately 75-95%, 80-90%, or 85% of an interior diameter of the main barrel.

It is contemplated that the gas flow alarm may include a first tab disposed on a proximal end of the cap and a channel defined by the main barrel. The first tab is configured to engage the channel when the cap is disposed on the main barrel. In alternative embodiments, the first tab may be two tabs (or more) and the channel may be two channels (or more).

In one embodiment of the gas flow alarm of the present invention, a second tab may be located on the main barrel at the proximal end. The second tab is contemplated to facilitate attachment of the main barrel to a gas source. The second tab may include two (or more) separate tabs.

Separately, to facilitate attachment of the main barrel to a gas source, the exterior surface of the main barrel may be configured to facilitate attachment of the main barrel to a gas source. In one embodiment, exterior surface of the main barrel may be textured, abraded, knurled, and shaped with a non-circular cross-section.

It is contemplated that the proximal end of the main barrel may include a gas pressure fitting.

In another embodiment, the main barrel and the cap may have cross-sectional shapes selected from circular, elliptical, square, triangular, rectangular, polygonal, ovoid, and amorphous.

It is contemplated that the main barrel and the cap are made from thermoplastics, resins, polymers, nylon, polyethylene, polytetrafluoroethylene, metal, and ceramics.

Still further aspects of the alarm of the present invention will be made apparent from the discussion that follows.

BRIEF DESCRIPTION OF THE DRAWINGS

The present invention will now be described in connection with the various figures appended hereto, in which:

FIG. 15 is a perspective illustration of the main barrel portion of the embodiment of the alarm illustrated in FIG. 1, the perspective being taken from the distal end.

DETAILED DESCRIPTION OF PREFERRED EMBODIMENT(S) OF THE INVENTION

The present invention will now be described in connection with one or more embodiments. The discussion of any one embodiment is not intended to be limiting of the present invention. To the contrary, the discussion of various embodiments is intended to illustrate the scope and breadth of the present invention. After reading and understanding the discussion that follows, those skilled in the art may contemplate one or more variations and equivalents to the embodiments discussed herein. Those variations and equivalents are intended to be encompassed by the present invention as if specifically described herein.

One embodiment of the alarm 10 of the present invention is illustrated in FIGS. 1-15.

Figure 1:
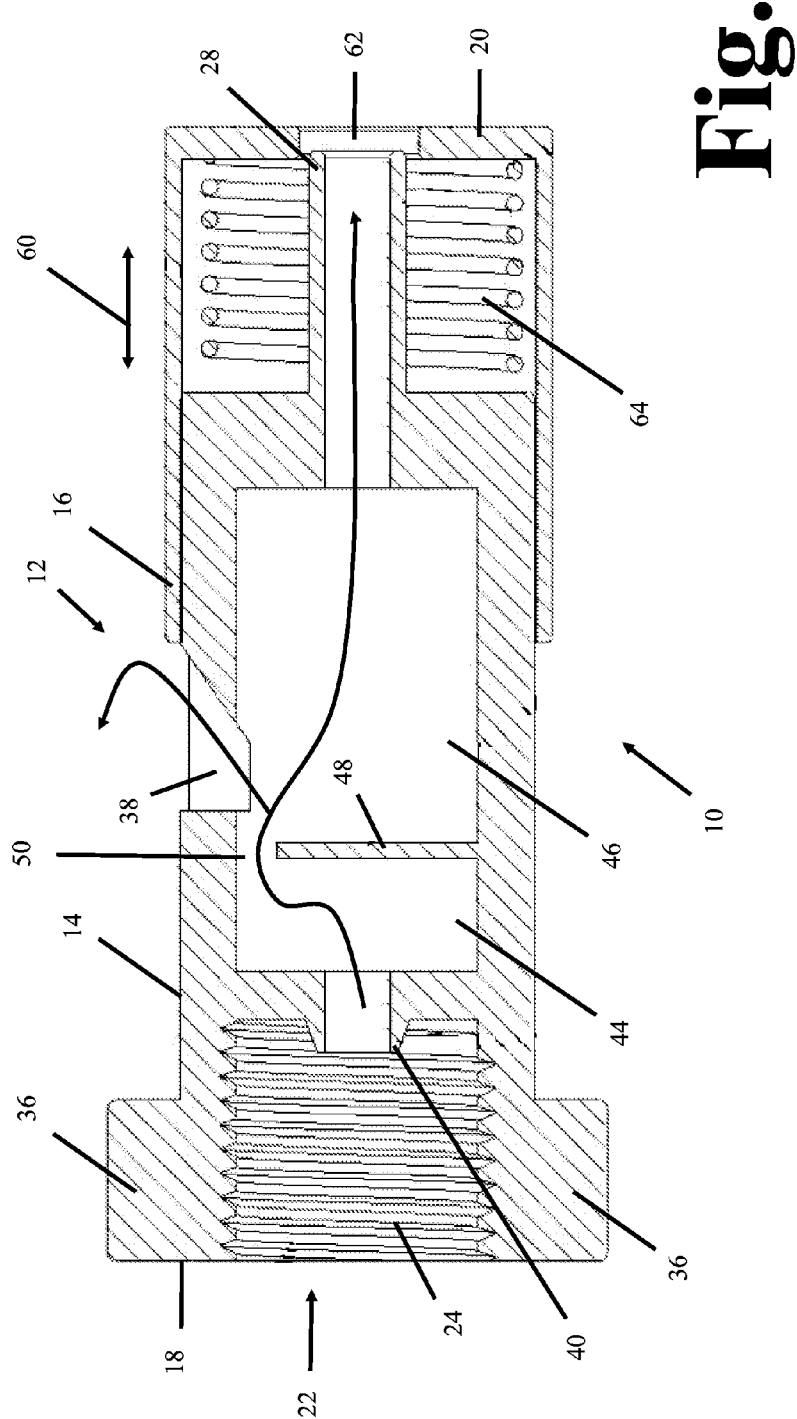
FIG. 1 is cross-sectional side view of one contemplated embodiment of the alarm of the present invention, shown in a fully assembled, expanded condition.

With reference to FIG. 1, the alarm 10 includes a body 12 with a main barrel 14 onto which a cap 16 is slidably disposed. In the illustrated embodiment, the body 12 has a cylindrical shape. Accordingly, the barrel 14 and the cap 16 also have cylindrical shapes.

While the alarm 10 is shown with a cylindrical shape, it is contemplated that the alarm 10 may have any alternative cross-sectional shape (e.g., elliptical, square, triangular, rectangular, polygonal, ovoid, amorphous, etc.) without departing from the scope of the present invention.

As a preliminary matter, it is noted that the various components of the alarm 10 of the present invention are contemplated to be made primarily from plastic materials. Alternatively, the alarm may be made from other materials, such as thermoplastics, resins, polymers, nylon, polyethylene, polytetrafluoroethylene, metal, ceramics, and/or any of a combination of these materials, among others. While it is contemplated that the alarm may be made primarily of polyethylene, the alarm 10 may be made from any suitable material without departing from the scope of the present invention.

As illustrated in FIG. 1 and as described in greater detail below, the alarm 10 of the present invention defines two ends, a first end 18 and a second end 20. The first end 18 also is referred to herein as the proximal end 18 of the alarm 10. The second end 20 also is referred to as the distal end 20. The proximal end 18 includes a threaded portion 22 (described in greater detail below) with female threads 24 that permits the alarm 10 to be attached to a Diameter Index Safety System ("D.I.S.S." or "DISS") connector 26 (e.g., shown in FIG. 2). The distal end 20 includes a nipple 28 to which tubing 30 may be attached for transporting the gas from the gas source 32 to the gas destination 34 (e.g., shown in FIG. 2).

The gas source 32 may be any suitable pressurized source of one or more gases. It is contemplated that the gas source 32 will be provided with (or connected to) the DISS connector 26. The DISS connector 26, in turn, is contemplated to engage the threads 24 in the proximal end 18 of the alarm 10.

The gas source 32 may be a gas container or canister, such as an oxygen cylinder. While a gas canister is contemplated as one potential gas source 32, it is noted that the source of the gas (or gases) may be a compressor or the like. Moreover, it is contemplated that the gas source 32 may provide a singular gas (such as oxygen) or a mixture of a plurality of gases (such as compressed air), without departing from the scope of the present invention. The gas source 32 also is contemplated to encompass several separate sources of gases that are combined prior to introduction of the gases into the alarm 10.

It is noted that the terms "proximal" and "distal" are employed herein in association with the gas source 32. Accordingly, the proximal end 18 of the alarm 10 is the end of the alarm 10 closest to the gas source 32. The distal end 20 of the alarm 10, therefore, is disposed furthest from the gas source 32. In this arrangement, the distal end 20 is downstream of the proximal end 18. As should be apparent, however, these terms are employed merely to facilitate a discussion of the alarm 10 of the present invention. The terms are, therefore, not intended to limit the scope of the present invention.

The tubing 30 may be any suitable tubing without departing from the scope of the present invention. In the case where oxygen passes through the alarm 10, it is contemplated that the tubing 30 may include a flexible, transparent segment that connects to a distributor, such as a nasal cannula for use by a medical patient. The tubing 30 may be made from any suitable material, as desired or required for a particular installation. The tubing 30 may be made from a single material. Alternatively, the tubing 30 may include multiple segments connected to one another, where the segments are each made from different materials.

The gas destination 34 includes devices that receive the gas provided by the gas source 32. One contemplated gas destination 34 is the nasal cannula, as noted above. Other gas destinations 34 include, but are not limited to, nozzles, acetylene torches, etc.

Figure 2:
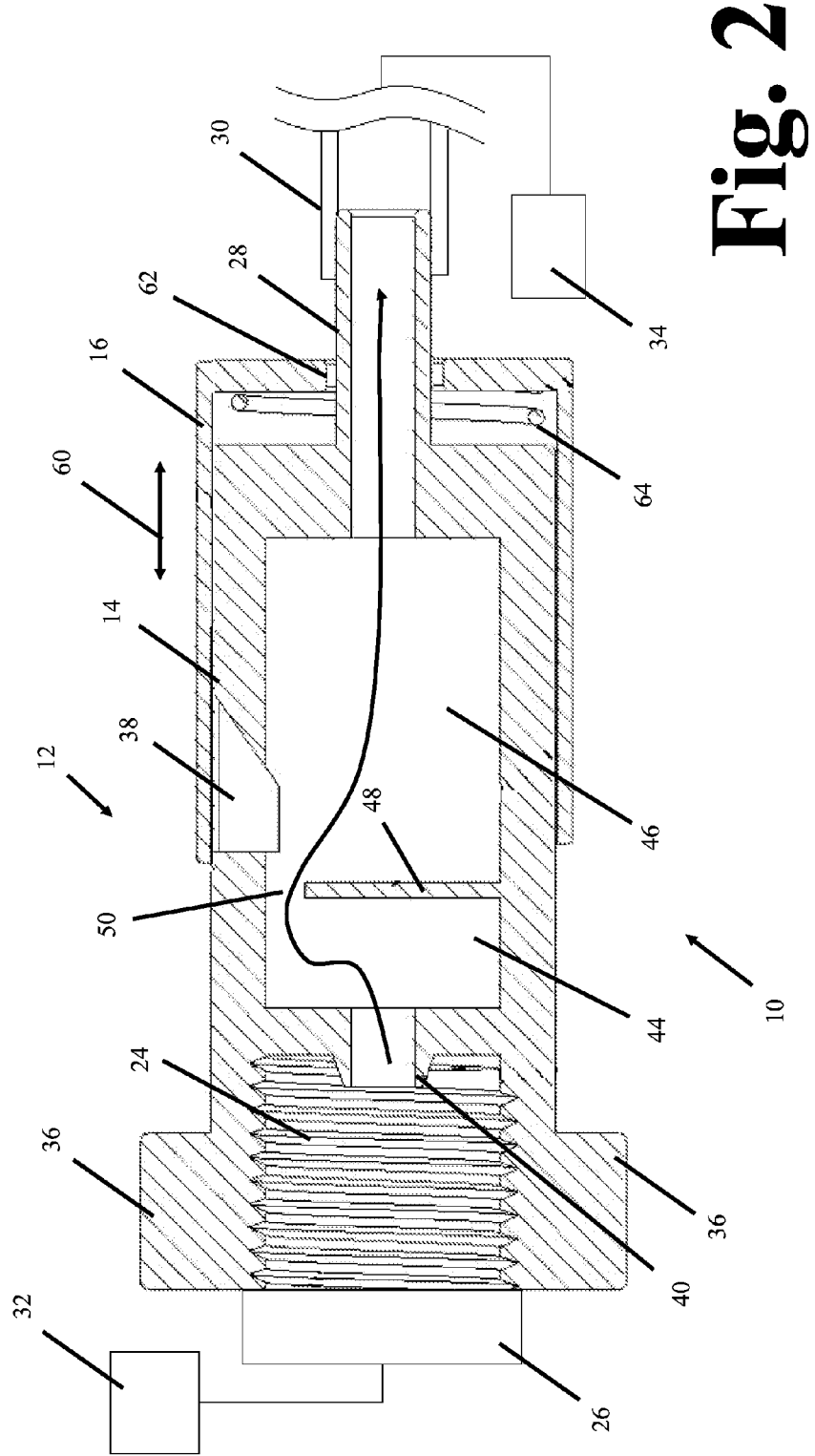
FIG. 2 is a cross-sectional side view of the embodiment of the alarm illustrated in FIG. 2, shown in a fully assembled, compressed condition.
Figure 3:
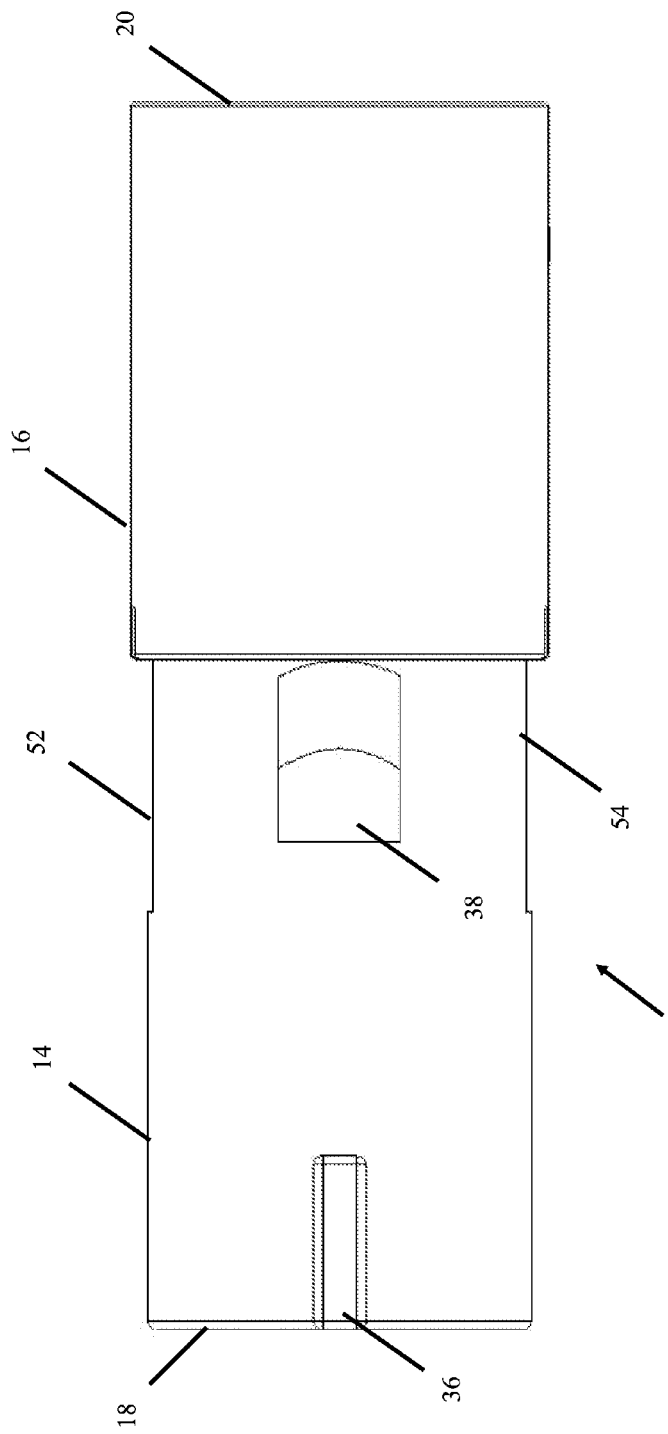
FIG. 3 is a top view of the embodiment of the alarm illustrated in FIG. 1, shown in the fully assembled, expanded condition.
Figure 4:
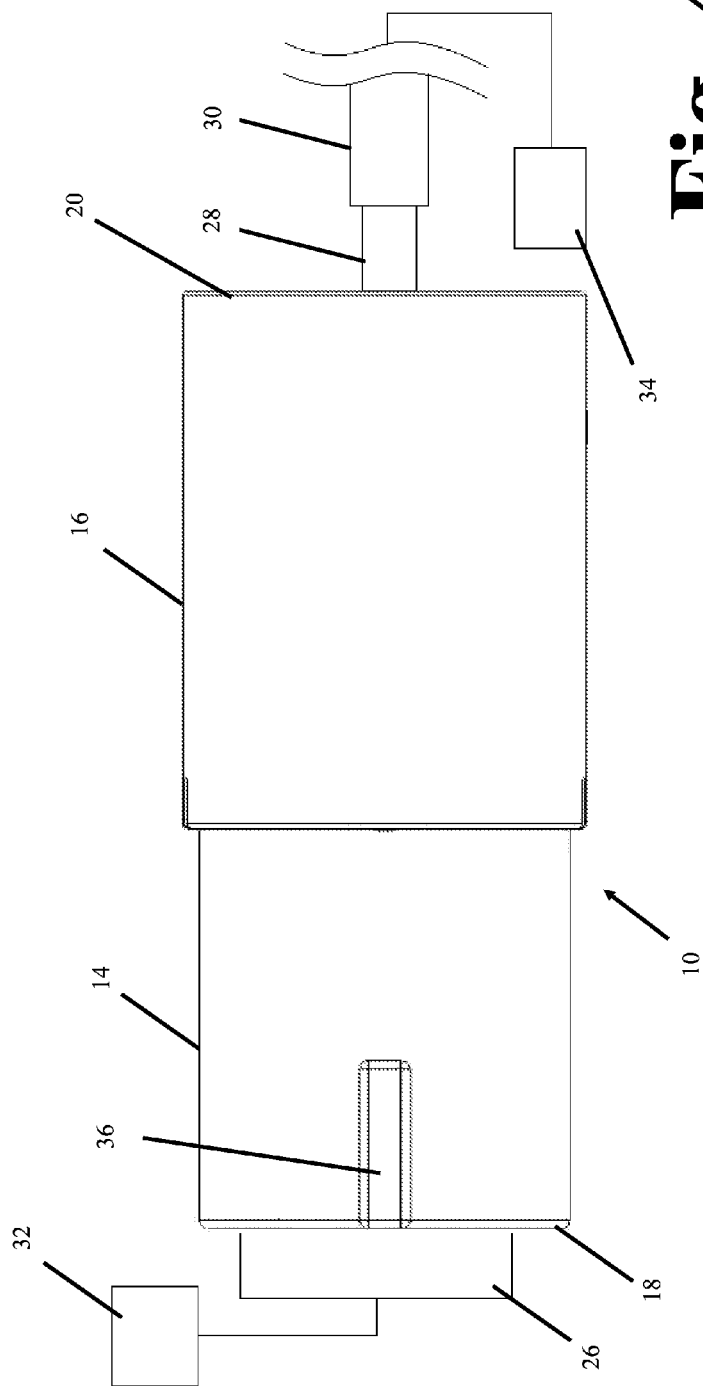
FIG. 4 is a top view of the embodiment of the alarm illustrated in FIG. 1, shown in the fully assembled, compressed condition.
Figure 5:
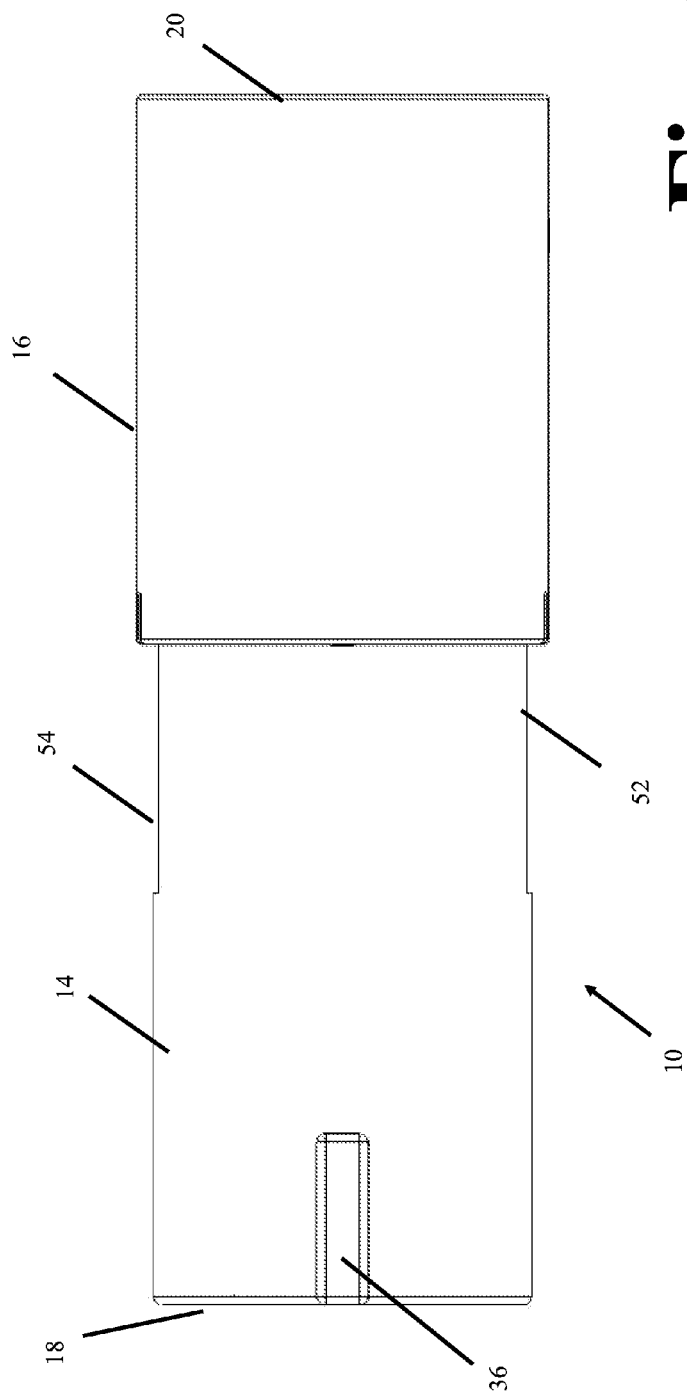
FIG. 5 is a bottom view of the embodiment of the alarm illustrated in FIG. 3, shown in the fully assembled, expanded condition.

The main barrel 14 of the body 12 includes at least two tabs 36 (also referred to as "leverage tabs" 36) that assist with installation of the alarm 10 to the DISS connector 26. The tabs 36 are contemplated to be positioned on opposite sides of the main barrel 14, opposite to one another, at the proximal end 18. FIGS. 1 and 2 illustrates this positioning. It is noted that, while the alarm 10 is shown with two tabs 36, the alarm 10 may include a larger or a fewer number of tabs 36 without departing from the scope of the present invention.

In addition, while the tabs 36 are illustrated at the proximal end 18 of the alarm 10, it is noted that the tabs 36 may be positioned at any location on the barrel 14 without departing from the scope of the present invention. As noted, the tabs 36 are provided to assist with threading the alarm 10 onto a suitable connector, such as a DISS connector 26.

While it is contemplated that the positioning of the tabs 36 at the proximal end 18 of the alarm 10 will best facilitate this operation, other locations are equally suitable for this purpose, as should be apparent to those skilled in the art.

In an alternate embodiment, the tabs 36 may be omitted altogether. Here, it is contemplated that the surface of the barrel 14 may be textured to establish an area on the barrel 14 that is easily gripped by a person. For example, the barrel 14 and cap 16 may have a non-circular cross-section, as noted above. Still further, the surface of the barrel 14 may be abraded so that it is not smooth or slippery to the touch. It is also contemplated that the surface of the barrel 14 may be provided with a knurled surface to establish a suitable grip thereon.

In still another contemplated embodiment, the alarm 10 may incorporate both the tabs 36 and a textured surface (i.e., a knurled or abraded surface), as required or as desired. It is noted that the tabs 36 are not required to practice the present invention. Moreover, a shaped and/or textured surface is not needed to practice the present invention.

FIG. 1 also illustrates a whistle 38 disposed through the side of the barrel 14. The whistle 38 is contemplated to generate an audible signal when gases pass through the body 12 and the cap 16 is in the extended condition illustrated in FIG. 1. In the extended condition, the whistle 38 is exposed. As a result, any gases passing through the barrel 14 will initiate a whistling sound when passing by the whistle 38.

FIG. 2 differs from FIG. 1 in that the alarm 10 in FIG. 1 is illustrated in the extended condition while the alarm 10 FIG. 2 is shown in the compressed condition. In the compressed condition, the whistle 38 is not exposed. In the compressed condition, the whistle 38 is covered by the cap 16. As a result, and gases passing through the main barrel 14 will not initiate a whistling sound.

With continued reference to FIGS. 1 and 2, it is noted that the main barrel 14 includes a gas pressure fitting 40 at the distal end of the threads 24. The gas pressure fitting 40 is provided to cooperate with the DISS connector 26. The gas pressure fitting 40 also may include one or more seals to facilitate a pressure-tight connection between the main barrel 14 and the DISS connector 26. As should be apparent to those skilled in the art, any suitable fitting 40 may be employed without departing from the scope of the present invention.

The main barrel 14 defines a central chamber 42 that is divided into a first chamber 44 and a second chamber 46 by a wall 48. Consistent with the terminology employed above, the first chamber 44 also is referred to as the proximal chamber 44. The second chamber 46 also is referred to herein as the distal chamber 46.

As illustrated, it is contemplated that the wall 48 is disposed immediately upstream of the whistle 38. In this position, the wall 48 directs the flow of gases through the chamber 42 such that the gas flow is concentrated at a position near to the whistle 38 to maximize the probability that the whistle 38 will generate an audible alarm. As should be apparent, without the wall 48, it is possible for the flow rate of gases from the gas source 32 might be so low that an audible alarm cannot be initiated. The wall 48 concentrates the flow of gases at the whistle 38 so that even a very low gas flow becomes sufficient to generate an audible alarm.

In the illustrated embodiment, the wall 48 is contemplated to extend to a height (or depth) within the central chamber 42 such that all but about 15% of the central chamber 42 is occluded. As noted, the portion of the central chamber 42 that is not occluded by the wall 48 is adjacent to the whistle 38. The wall 48, therefore, defines an opening 50 within the central chamber 42 that is approximately 15% of the interior diameter of the central chamber 42. It is noted that the wall 48 need not provide an opening 50 that is 15% of the interior diameter of the central chamber 42. A larger or a smaller opening 50 may be established within the scope of the present invention. For example, it is contemplated that the opening 50 may be between 5-25% of the interior diameter in one embodiment. In another embodiment, the opening 50 may be 10-20% of the interior diameter of the central chamber 42.

With respect to the opening 50, it is noted that the interior chamber 42 may have a shape other than a circular shape, as provided in the illustrated embodiment. If so, the size of the opening 50 is contemplated to be adjusted accordingly, as should be apparent to those skilled in the art.

As illustrated throughout the figures, it is contemplated that the main barrel 14 is completely hollow, thereby defining the central chamber 42. As illustrated, only the wall 48 is disposed within the central chamber 42. While this embodiment is illustrated, it is contemplated that the central chamber 42 need not be entirely hollow. The central chamber 42 may be partially occluded in other ways to improve or alter the flow of gases therethrough.

Figure 6:
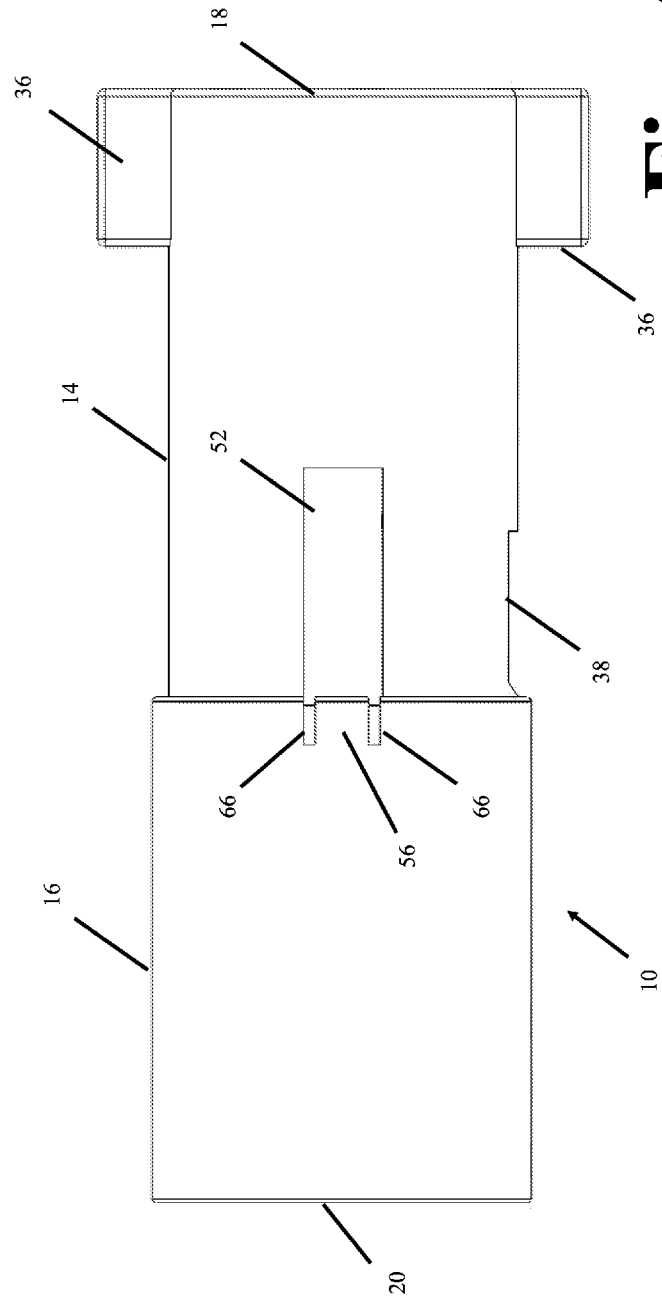
FIG. 6 is a left side view of the embodiment of the alarm illustrated in FIG. 1, shown in the fully assembled, expanded condition.
Figure 7:
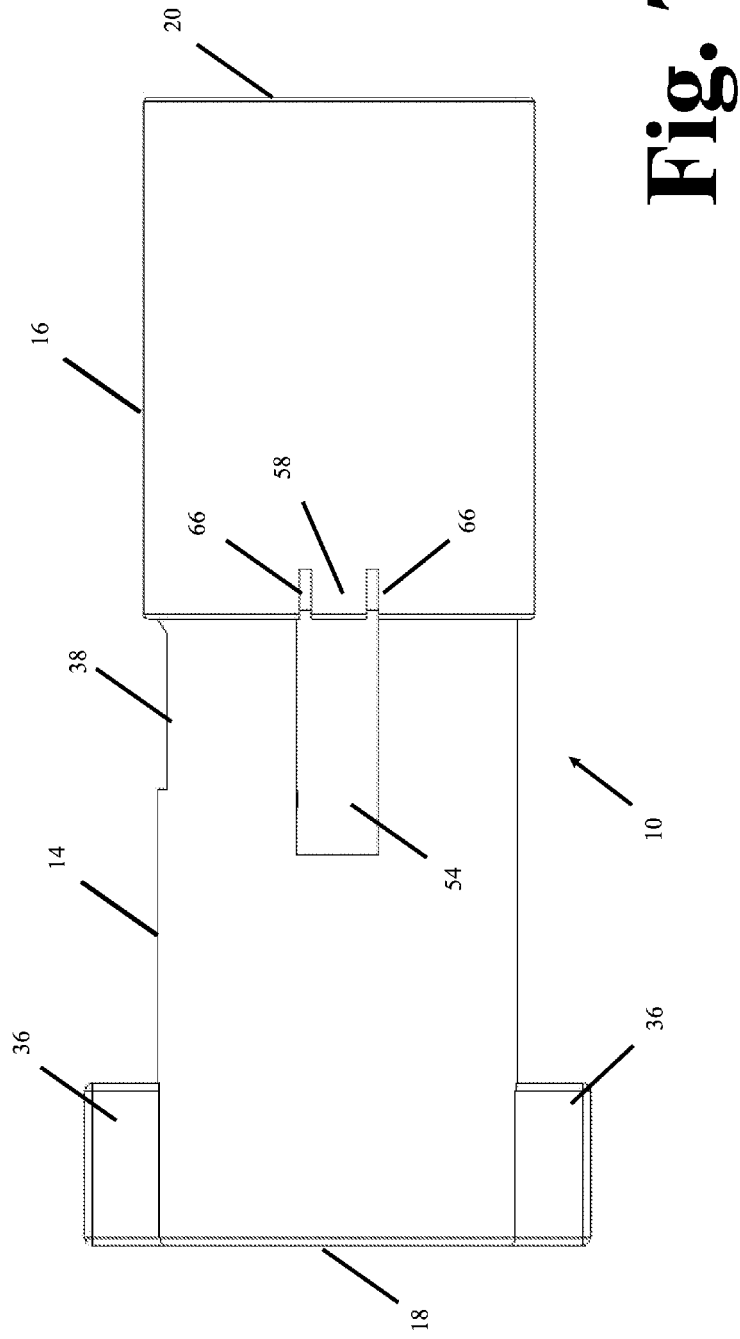
FIG. 7 is a right side view of the embodiment of the alarm illustrated in FIG. 1, shown in the fully assembled, expanded condition.

So that the alarm 10 may transition between the expanded condition illustrated in FIG. 1 and the compressed condition illustrated in FIG. 2, the main barrel 14 includes a first channel 52 and a second channel 54. The channels 52, 54 are provided so that the cap 16 slidably engages the main barrel 14. In particular, as illustrated in FIGS. 6 and 7, the cap 16 is provided with tabs 56, 58 that engage the channels 52, 54, by extending into the channels 52, 54 by a predetermined distance. Cooperation between the channels 52, 54 and the tabs 56, 58 assist to hold the cap 16 onto the main barrel 14. Cooperation between the channels 52, 54 and the tabs 56, 58 also assist to permit the cap to slide with respect to the main barrel 14, as indicated by the arrows 60.

At the distal end of the main barrel 14, a nipple 28 extends axially through the center of the cap 16. The nipple 28, after being exposed from the cap 16 when the alarm 10 is in the compressed condition, is provided to engage the tubing 30. While the nipple 28 is contemplated to be cylindrical, the nipple 28 need not be cylindrical to practice the present invention. In addition, the nipple 28 is illustrated as being coaxial with the main barrel 14. While this is contemplated for the illustrated embodiment, the nipple 28 may be offset from the axis of the main barrel 14 without departing from the scope of the present invention.

With respect to the construction of the main barrel 14 and the nipple 28, the two parts of the alarm 10 are contemplated to be integrally formed with one another. As should be apparent, however, an integral construction is not required to practice the present invention. The nipple 28 may be manufactured separately from the main barrel 14 and attached to the main barrel 14 during assembly.

With continued reference to FIG. 1, for example, the cap 16 is provided with an opening 62 in the distal end thereof. The opening 62 is provided so that the nipple 28 may protrude exterior to the cap 16 when the alarm 10 is in the compressed condition. This permits attachment of the tubing 30, as illustrated in FIG. 2, for example.

As also illustrated in FIG. 1, the alarm 10 includes a biasing member 64, which is contemplated to bias the cap 16 so that the alarm 10 defaults to the expanded condition when the tubing 30 is removed from the nipple 28. While the biasing member 64 is illustrated as a coil spring, any other type of biasing member may be employed without departing from the scope of the present invention.

The operation of the alarm 10 will now be discussed in connection with FIGS. 1 and 2.

It is noted that the alarm 10 is constructed to be added in the gas flow path downstream of the gas source 32 and upstream of the gas destination 34. Installation of the alarm 10 on the DISS connector 26 is contemplated to be via hand tightening, using the tabs 36. The cap 16 is pushed in the proximal direction so that the alarm 10 is configured in the compressed condition, which is illustrated in FIG. 2. The tubing 30 is then attached to the nipple 28, which protrudes through the opening 62. In the compressed state, the cap 16 covers the whistle 38, thereby inhibiting the whistle 38 from issuing an audible alarm.

Should the tubing 30 become disconnected from the nipple 28, the biasing member 64 will force the cap 16 in the distal direction. When the cap 16 is pushed into the expanded condition, the whistle 38 is exposed. As a result, if there is sufficient gas flow through the main barrel 14 from the gas source 32, the alarm 10 will generate an audible signal via the whistle 38.

Figure 8:
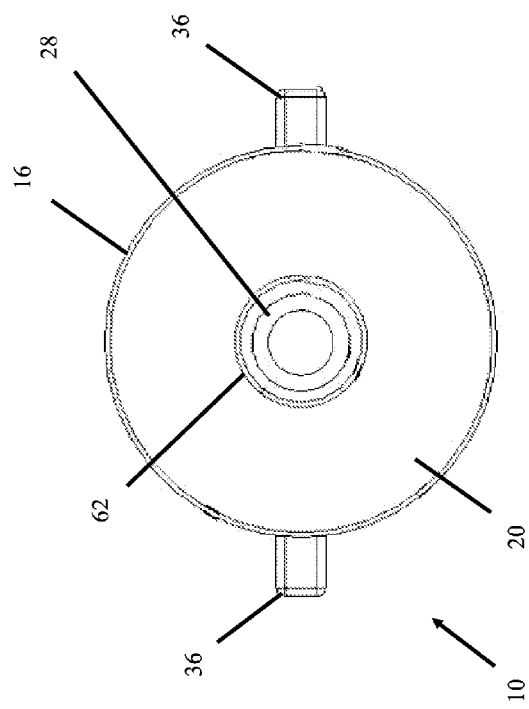
FIG. 8 is a view of the first end of the embodiment of the alarm illustrated in FIG. 1, with this first end also being referred to as the distal end of the alarm.

FIG. 8 is an end view of the alarm 10, the view being taken from the distal end of the alarm 10. The cap 16, nipple 28, and tabs 36 are clearly delineated in this view.

Figure 9:
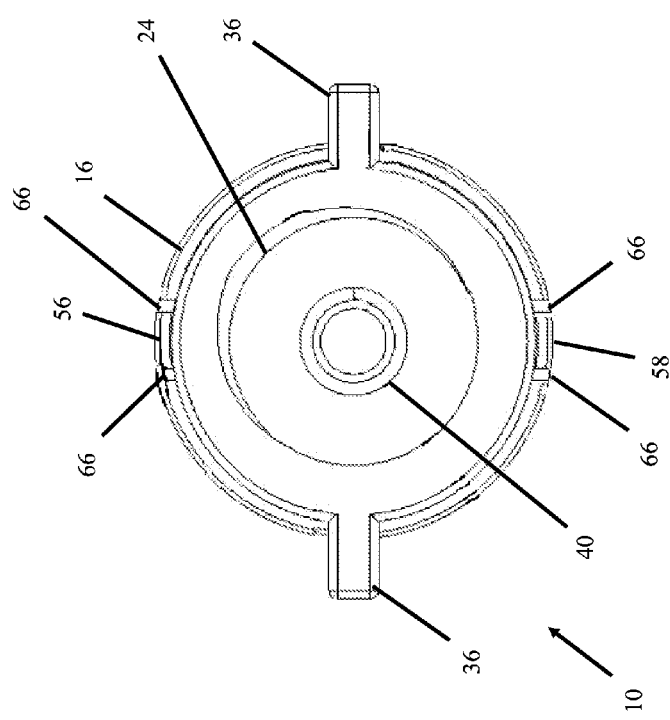
FIG. 9 is a view of the second end of the embodiment of the alarm illustrated in FIG. 1, with this second end also being referred to as the proximal end of the alarm.

FIG. 9 is an end view of the alarm 10 from the proximal end. The threads 24, pressure fitting 40 and tabs 36 are easily visible in this view.

Figure 10:
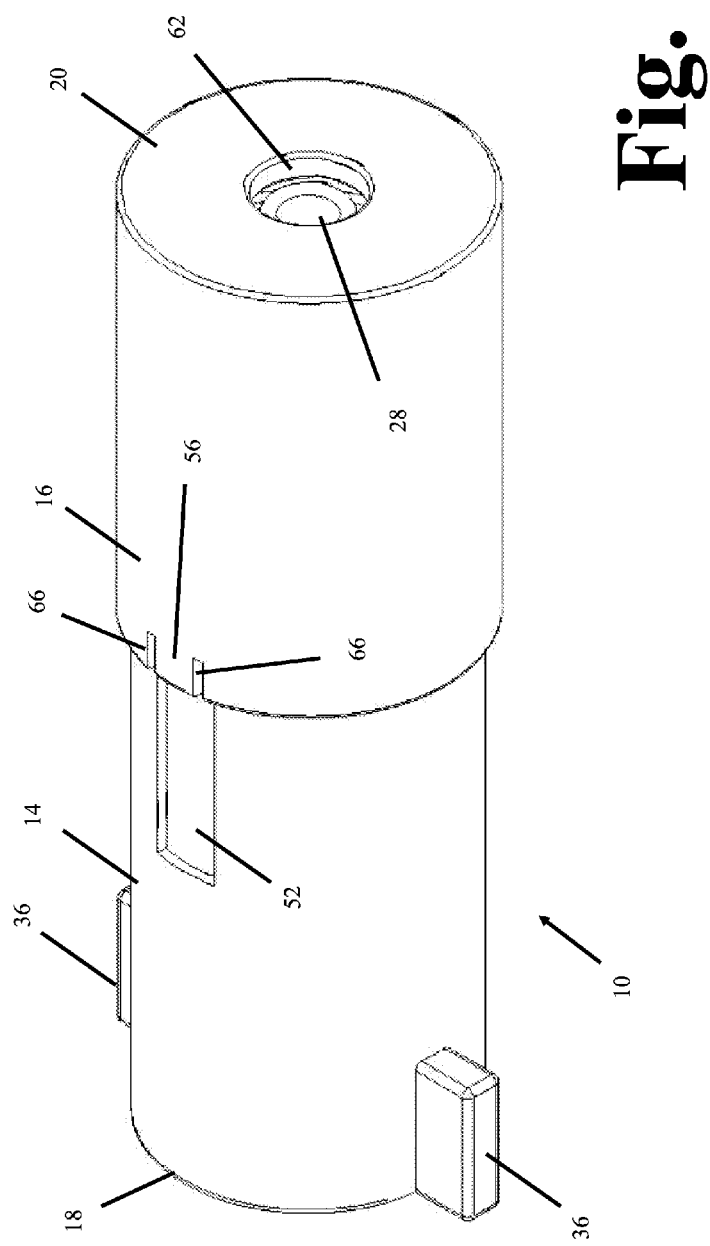
FIG. 10 is a perspective illustration of the embodiment of the alarm shown in FIG. 1, the perspective being from the first or distal end thereof, the alarm being shown in the fully assembled, expanded condition.

FIG. 10 is a perspective view of the alarm 10 of the present invention. The perspective is taken from the distal end of the alarm 10.

Figure 11:
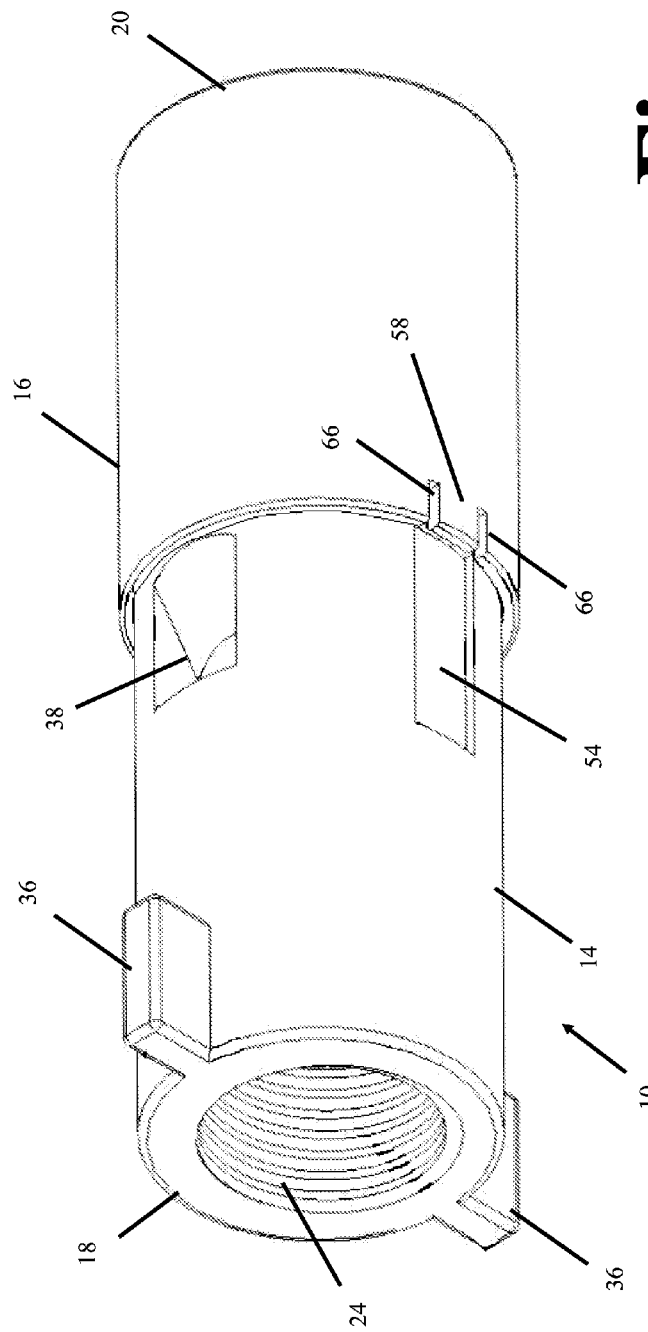
FIG. 11 is a perspective illustration of the embodiment of the alarm shown in FIG. 1, the perspective being from the second or proximal end thereof, the alarm being shown in the fully assembled, expanded condition.

FIG. 11 is a perspective view of the alarm 10 of the present invention. The perspective is taken from the proximal end of the alarm 10.

Figure 12:
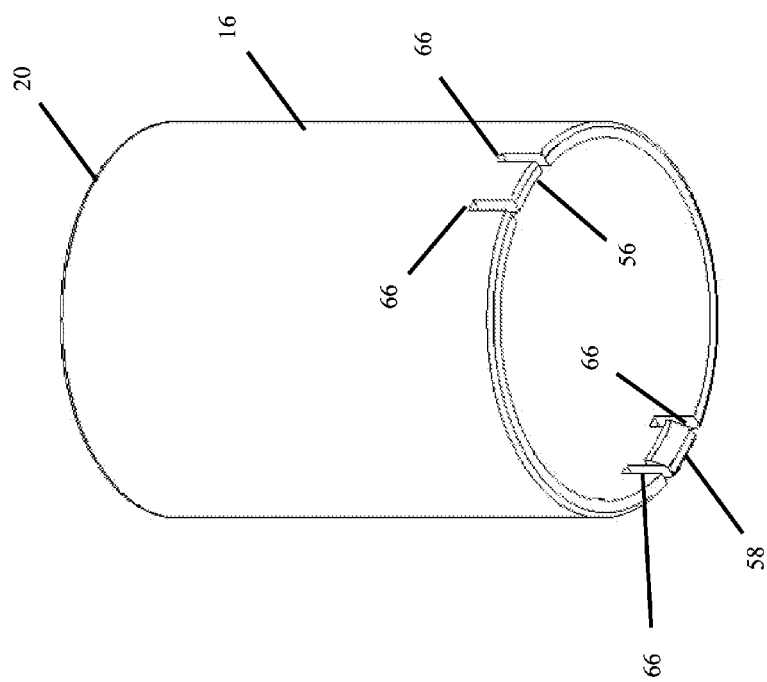
FIG. 12 is a perspective illustration of the cap that forms a part of the embodiment of the alarm shown in FIG. 1, the perspective being from a bottom end thereof.

FIG. 12 is a perspective illustration of the cap 16 from the alarm 10. The perspective is taken from the proximal end of the cap 16.

Figure 13:
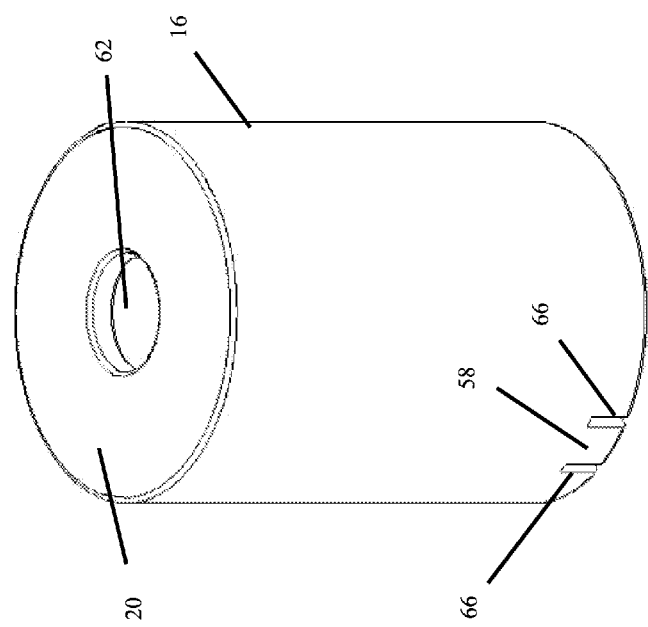
FIG. 13 is a perspective illustration of the cap shown in FIG. 12, the perspective being taken from the top end thereof.

FIG. 13 is a perspective illustration of the cap 16, taken from the distal end. One of the tabs 56 is visible in this illustration. As also shown in this view (among others) the tab 56 is bounded on either side by slots 66 that provide flexibility to the tab 56 so that is may more easily engage the channel 52. The tab 58 is similarly bounded by slots 66. It is noted that, depending upon the material selected for manufacture of the cap 16, the slots 66 may not be required to practice the present invention.

Figure 14:
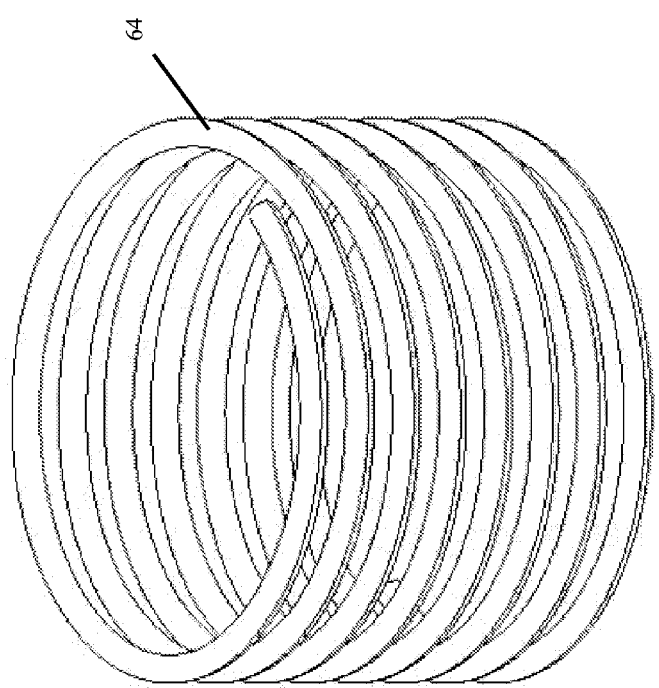
FIG. 14 is a perspective illustration of a biasing member employed in the embodiment of the alarm illustrated in FIG. 1.

FIG. 14 is a perspective illustration of the biasing member 64, which assists to bias the cap 16 so that the alarm 10 defaults to the expanded condition, as discussed above.

FIG. 15 is a perspective illustration of the main barrel 14 and nipple 28, illustrated from the distal end thereof.

With further reference to the nipple 28, it is noted that the nipple 28 may be any of a number of different shapes and configurations without departing from the scope of the present invention. Moreover, the nipple 28 may have any size suitable for the tubing 30. In addition, the nipple 28 may be provided with threads (either external (male) or internal (female)) for engagement with a suitable fitting, as required or as desired. If provided with male threads, the nipple 28 may be designed consistently with the construction of the DISS connector 26, thereby providing the same connector as occupied by the threads 24 on the proximal end 18 of the alarm 10.

With regard to the channels 52, 54, it is noted that the channels 52, 54 are illustrated as being disposed on opposite sides of the main barrel 14. As should be apparent, the main barrel 14 may be provided with a larger or a fewer number of channels 52, 54 without departing from the scope of the present invention. Moreover, while the channels 52, 54 are illustrated as being disposed 180° from one another, they may be positioned at any location with respect to one another without departing from the scope of the present invention. In addition, it is noted that the channels 52, 54 are shown in positions that are 90° from the position of the whistle 38. While this is contemplated as one possible orientation of the channels 52, 54 with respect to the whistle 38, any other alternative orientation may be employed without departing from the scope of the present invention. Finally, the channels 52, 54 are contemplated to extend along most of the length of the main barrel 14. As should be apparent, however, the lengths and shapes of the channels 52, 54 may be altered without departing from the scope of the present invention.

As should be apparent to those skilled in the art, as has been made apparent from the foregoing, the inner diameter (ID) of the cap 16 is larger than the outer diameter (OD) of the main barrel 14. As such, the cap 16 may slide, in the direction of the arrows 60, with respect to the main barrel 14. It is contemplated that the inner surface of the cap 16 will engage the outer surface of the main barrel 14 to provide at least a minimal seal therebetween. Alternatively, one or more sealing members may be positioned between the inner surface of the cap 16 and the outer surface of the main barrel 14 to establish whatever magnitude of sealing capacity is required or desired.

With respect to the opening 62 in the cap 16, it is contemplated that the opening will have an ID slightly larger than the OD of the nipple 28. In the case where the nipple 28 does not have a cylindrical shape, the opening 62 will be patterned to accommodate the shape of the nipple 28.

It is contemplated that the tabs 56, 58 will engage the channels 52, 54 such that the tabs 56, 58 fit in the channels 52, 54. The tabs 56, 58, therefore, prevent the cap 16 from becoming dislodged from the main barrel 14. Specifically, the tabs 56, 58, when inserted into the channels 52, 54 are bound by the lengths of the channels 52, 54. As such, the cap 16 is not easily removed from the main barrel 14 after the tabs 56, 58 have been inserted into the channels 52, 54. As should be apparent from the foregoing and from the illustrations, the cap 16 is contemplated to be removable from the main barrel 14 after application of a sufficient force to the cap 16 or the tabs 56, 58. In other words, it is contemplated that the cap 16 is removable from the main barrel 14 when required or desired.

As made apparent from the foregoing, the alarm 10 of the present invention is not intended to be limited to the particular embodiment(s) detailed herein and illustrated in the accompanying figures of the drawings. As will be appreciated by those skilled in the art, various embodiments of the alarm 10 may be constructed that incorporate selected ones of the advantages and structures described herein.

The figures of the drawings are intended to illustrate the general characteristics of structures described in connection with the embodiment(s) and to supplement the written description associated with the alarm 10. In connection therewith, the figures are not drawn to scale and, therefore, are not intended to reflect the precise structural or performance characteristics of any given embodiment. Moreover, the drawings should not be interpreted as defining or limiting the range of values or properties encompassed by any enumerated embodiment. Each of the embodiments, however, is contemplated to incorporate structures permitting the alarm 10 to alert people or practitioners in the immediate area of the alarm 10 that gas is leaking into the ambient air (or surrounding environment).

As will be appreciated by those skilled in the art, there are many variations that may be employed that are contemplated to accomplish the same results as the embodiment(s) of the alarm 10 described herein. For example, the materials selected for construction of the ambient gas flow alarm 10 may include any number of readily available polymers, ceramics and/or metals, as noted above. Similarly, the alarm 10 need not be separate from the gas source 32. To the contrary, the alarm 10 may be integrated into any gas flow device connected to (or a part of) the gas source 32, whether the gas flow device is independent from the gas source 32 integrated into any structure known to one of ordinary skill in the art that is a part of the gas source 32. Further, a wide range of assembly structures, e.g., recesses and corresponding projections, set screws, welds, pins, etc., easily may be utilized for locating the various structural elements of the ambient gas flow alarm 10 without departing from the basic functionality of the devices detailed herein.

As should be appreciated from the foregoing, the ambient gas flow alarm 10, consistent with the present invention, is contemplated to be configured for at least the following:

1) creating an audible alarm while the flow of gas is being released into the ambient room air exposing objects in the immediate air to the gas;

2) creating an audible alarm when the flow of gas is being released into the ambient room air causing a waste of resources and expenses; and 3) creating an alarm when a device that is connected to the nipple 28 has inadvertently become disconnected.

Any and all variations to the designs disclosed herein that accomplish these three functions, among others, are considered to be within the scope of this disclosure. None of the variations, however, are contemplated to detract from the basic functionality of the disclosed embodiments of the alarm 10 of the present invention.

When the alarm 10 of the present invention is attached to a gas source 30 and has gas flowing therethrough and the alarm 10 is in the extended condition, the whistle 38 makes a whistling sound alerting people in proximity to the alarm 10 that gas is flowing in a manner inconsistent with normal usage of the gas. The whistling may be stopped by turning off the source 32 of the flowing gas. The whistle 38 is closed, as noted above, by sliding the cap 16 over the whistle 38, thereby directing the gas through the nipple 28. If the tubing 30 (or any gas destination 34) becomes disconnected from the nipple, the biasing member 64 causes the alarm 10 to configure itself in the expanded condition. The alarm 10 may be returned to the compressed condition by pressing on the cap 16. In the expanded condition, the whistle 38 is exposed, resulting in the generation of the audible alarm.

As noted above, the alarm 10 may include one or more seals to minimize the release of gases from the alarm 10 during use. This includes one or more seals between the cap 16 and the main barrel 14. In addition, the alarm 10 may include one or more stoppers to plug the whistle 38 when the cap 16 is disposed toward the proximal end of the device and the alarm 10 is in the compressed condition.

As should be apparent, while a whistle 38 is contemplated as an aspect of the present invention, any other suitable noise generating device may be employed without departing from the scope of the present invention. In addition, the present invention should not be considered to be limited solely to the embodiment(s) described herein. As noted above, the present invention is contemplated to encompass any equivalents and variations of the embodiment(s) described herein.

What is claimed is:

1. A gas flow alarm, comprising:
   a main barrel with a proximal end and a distal end, wherein the main barrel defines a gas flow direction from the proximal end to the distal end;
   a cap slidingly disposed on the main barrel between a proximal position and a distal position, wherein the proximal position of the cap defines a compressed condition of the gas flow alarm and the distal position of the cap defines an expanded condition of the gas flow alarm; and
   a noise generating device disposed within the main barrel, wherein the noise generating device is adapted to generate noise from the gas flow when the gas flow alarm is in the expanded condition.

2. The gas flow alarm of claim 1, wherein the noise generating device is a whistle.

3. The gas flow alarm of claim 1, further comprising:
   a biasing member operatively disposed between the cap and the main barrel, biasing the cap in the distal position.

4. The gas flow alarm of claim 3, wherein the biasing member is a coil spring.

5. The gas flow alarm of claim 1, wherein the proximal end of the main barrel defines a threaded portion.

6. The gas flow alarm of claim 5, wherein the threaded portion is adapted to accommodate a diameter index safety system connector.

7. The gas flow alarm of claim 6, wherein the diameter index safety system connector is connected to a gas source.

8. The gas flow alarm of claim 1, further comprising:
   a nipple disposed at the distal end of the main barrel for connection to a gas destination.

9. The gas flow alarm of claim 8, wherein the gas destination comprises tubing.

10. The gas flow alarm of claim 8, wherein the cap defines an opening through a distal end thereof, permitting the nipple to protrude therethrough when the gas flow alarm is in the compressed condition.

11. The gas flow alarm of claim 1, further comprising:
    a wall disposed within the main barrel, upstream of the noise generating device, for concentrating the gas flow adjacent to the noise generating device, thereby enhancing the noise generated thereby.

12. The gas flow alarm of claim 11, wherein the wall occludes approximately at least one of 75-95%, 80-90%, and 85% of an interior diameter of the main barrel.

13. The gas flow alarm of claim 1, further comprising:
    at least one first tab disposed on a proximal end of the cap; and
    at least one channel defined by the main barrel,
    wherein the first tab is configured to engage the channel when the cap is disposed on the main barrel.

14. The gas flow alarm of claim 13, wherein the first tab comprises two tabs and the channel comprises two channels.

15. The gas flow alarm of claim 1, further comprising:
    at least one second tab disposed on the main barrel at the proximal end, the second tab facilitating attachment of the main barrel to a gas source.

16. The gas flow alarm of claim 15, wherein the second tab comprises two second tabs.

17. The gas flow alarm of claim 1, wherein an exterior surface of the main barrel is configured to facilitate attachment of the main barrel to a gas source.

18. The gas flow alarm of claim 17, wherein the exterior surface of the main barrel is at least one of textured, abraded, knurled, and shaped with a non-circular cross-section.

19. The gas flow alarm of claim 1, wherein the main barrel and the cap have cross-sectional shapes selected from circular, elliptical, square, triangular, rectangular, polygonal, ovoid, and amorphous.

20. The gas flow alarm of claim 1, wherein the main barrel and the cap are made from at least one of thermoplastics, resins, polymers, nylon, polyethylene, polytetrafluoroethylene, metal, and ceramics.

* * * * *